United States Patent [19]

Fanlo

[11] Patent Number: 5,178,157
[45] Date of Patent: Jan. 12, 1993

[54] PHLEBOTOMY DEVICE AND METHOD OF USE THEREOF

[76] Inventor: Ramon G. Fanlo, 13910 Baton Rouge Ct., Centerville, Va. 22020

[21] Appl. No.: 820,259

[22] Filed: Jan. 14, 1992

[51] Int. Cl.$^5$ .......................... A61M 5/00; A61B 17/00
[52] U.S. Cl. ..................................... 128/763; 128/760; 128/764; 604/172; 604/174
[58] Field of Search ......... 128/760, 763, 764, DIG. 6; 604/174, 177

[56] References Cited

U.S. PATENT DOCUMENTS

| | | |
|---|---|---|
| 2,955,595 | 10/1960 | Semple . |
| 4,116,066 | 9/1978 | Mehl et al. ............................ 128/760 |
| 4,324,236 | 4/1982 | Gordon et al. . |
| 4,326,519 | 4/1982 | D'Alo et al. ......................... 604/177 |
| 4,653,511 | 3/1987 | Goch et al. .......................... 128/763 |
| 4,676,783 | 6/1987 | Jagger et al. ........................ 604/177 |
| 4,690,675 | 9/1987 | Katz ..................................... 604/177 |
| 4,737,143 | 4/1988 | Russell ................................. 604/174 |
| 4,758,231 | 7/1988 | Habar et al. . |
| 4,875,896 | 10/1989 | Kurtz . |
| 4,947,863 | 8/1990 | Habar et al. . |
| 4,970,052 | 11/1990 | Oberhardt et al. .................. 128/763 |
| 5,086,780 | 2/1992 | Schmitt ................................. 128/760 |

FOREIGN PATENT DOCUMENTS 8909025 10/1989 World Int. Prop. O. .......... 128/763

Primary Examiner—Stephen C. Pellegrino
Assistant Examiner—Glenn Dawson
Attorney, Agent, or Firm—Richard C. Litman

[57] ABSTRACT

A phlebotomy device for taking blood samples and a method of use thereof. This blood collection device can be either self administered or administered by a health care professional. The device includes a stand and a complete disposable proboscis set. The stand facilitates the stable retention of the blood collection tube holder at an angle which ensures accurate and expedient filling of blood sample tubes and the reduction of forthing or aerating. This stand has an open bottom providing a means to apply a needle adapter to the blood collection tube holder, to apply a snout to the needle adapter, and to route the snout through a snout holder. The top of the stand includes a refillable needle disposal pit preferably comprised of hypochlorite clay. The needle adapter, having a needle insertable into a blood collection tube, and the snout are incorporated in the proboscis set. the proboscis set further includes a mosquito needle insertable into a patient's blood vessel, comprising a needle guard, plastic wings with stilt adhesive attached thereon, and a hub to accommodate the connection of the snout. The plastic wings are foldable and attachable to the arm of the patient and maintain the needle at an angle to ensure that the needle penetrates only the upper portion of the vein being punctured, and thus keeps it steadily in place.

12 Claims, 4 Drawing Sheets

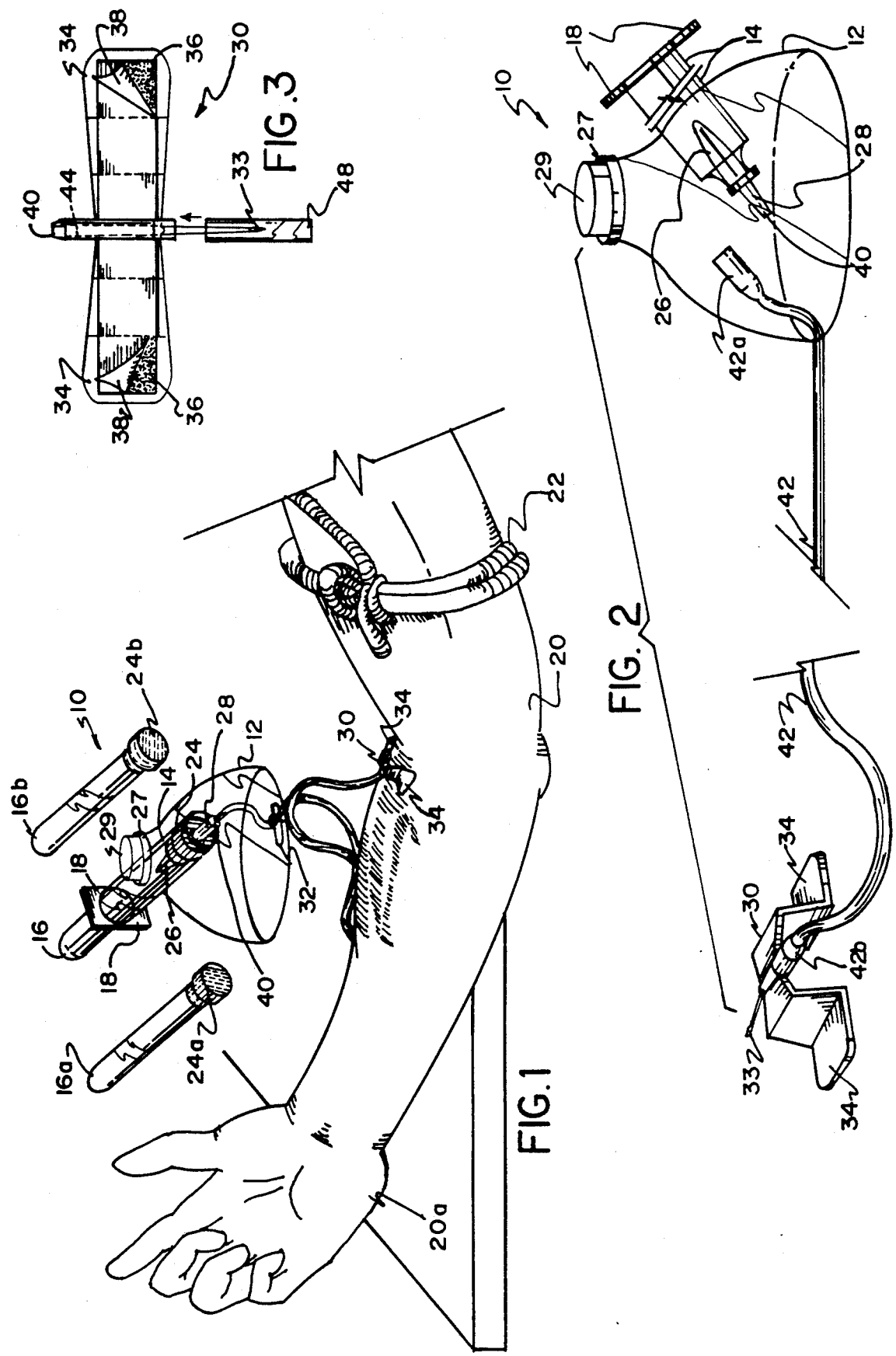

PHLEBOTOMY DEVICE AND METHOD OF USE THEREOF

BACKGROUND OF THE INVENTION

1. Field of the Invention

The present invention relates to a blood sampling device which allows a faster, more accurate phlebotomy to be either self administered or administered by a licensed health care professional.

2. Description of Prior Art

Hypodermic syringes are used for a variety use purposes, one of which is for a vacuum tube phlebotomy where successive samples of a patient's blood are drawn into respective evacuated tubes by way of a multiple sample needle. The syringe may be administered to a patient having a communicable disease. As a result, health care workers as well as the patients themselves are both at risk and are constantly threatened by accidental and potentially infectious needle strikes due to the handling and disposal of contaminated needles. Such accidents typically require the individual exposed to the needle strike to undergo routine costly tests for diseases such as AIDS and hepatitis.

There is a heightened awareness of the need to control infectious diseases when drawing blood samples from patients. This has inspired the incorporation of safety features into the design of many blood collection apparatuses. One such safety mechanism is the employment of needle shielding to reduce the risk of accidental needle strike. A common needle shielding device includes a protective sleeve which slides over a contaminated needle to surround and shield the needle after use. The passage into the sleeve, however, is of a very small diameter and the needle being inserted into the sleeve is very sharp. Consequently, the individual attempting to perform this task, especially under highly stressful situations, such as emergencies, is placed under a substantial amount of risk. Moreover, with shielding, there exists the tendency to splatter microdroplets of blood outside of the sleeve device into the surrounding environment. A phlebotomy device which could be self administered or which would reduce risk of exposure of potential needle strikes to health care workers could prove to be invaluable.

There are devices in existence which aid in reducing the risk of accidental needle strike. However, no device is in existence which aids in the self administration of a phlebotomy.

U.S. Pat. No. 2,955,595 issued Oct. 11, 1960 to Robert J. Semple discloses a fluid sampling device for the sterile handling of therapeutic fluids, as in the collecting of blood.

U.S. Pat. No. 4,324,236 issued Apr. 13, 1982 to Marvin Gordon et al. shows a fitting for use in performing a vascular puncture wherein a rapid and secure stabilization of an intravascular catheter or needle to a patient's skin upon insertion of the catheter or needle into a blood vessel is achieved.

U.S. Pat. No. 4,758,231 issued Jul. 19, 1988 to Terry Haber et al. describes a disposable syringe having a particular application to vacuum tube phlebotomy and comprising a needle shielding means to reduce the possibility of accidental needle strike.

U.S. Pat. No. 4,875,896 issued Oct. 24, 1989 to Sharon L. Kurtz discloses a needle disposal device for needles and a method for preventing accidental needle strike by a contaminated needle.

U.S. Pat. No. 4,947,863 issued Aug. 14, 1990 to Terry M. Habar et al. shows a disposable blood collection tube holder for administering a vacuum tube phlebotomy and a safe and reliable means to shield the needle after use to reduce the risk of accidental needle strike by a contaminated needle.

None of the above inventions and patents, taken either singly or in combination, is seen to describe the instant invention as claimed.

SUMMARY OF THE INVENTION

The present invention relates to a device for taking blood samples and a method of use thereof. With this blood collection device, a faster, more accurate phlebotomy or blood collection can be either self administered or administered by a health care professional. The phlebotomy device includes a stand to facilitate the stable retention of a blood collection tube holder at an angle which ensures a fast and accurate filling of blood sample tubes without frothing or aerating. This stand has an open bottom providing a means to threadably attach a needle adapter to the blood collection tube holder, a means to engage a snout with the needle adapter, and a means to route the snout through a snout holder. The top of the stand includes a refillable needle disposal pit comprised of a pliable substance such as hypochlorite clay. The needle adapter, having a needle insertable axially into a blood collection tube, and the snout or plastic tube are incorporated in a proboscis set. The proboscis set further includes a mosquito needle insertable into a patient's blood vessel and comprising a needle guard, plastic wings with stilt adhesive attached thereon, and a hub to accommodate the connection of the snout.

The phlebotomy device is particularly useful for self administration applications. The method of use of the device follows the conventional preliminary preparation steps of washing the hands, applying the tourniquet to locate the puncture site, removing the tourniquet once the site is located, and cleansing the site with alcohol. Once these steps have been completed, reapply the tourniquet, insert the mosquito needle into the vein, expose the stilt adhesive, and allow the stilt adhesive to stick to the skin, fixing the mosquito needle in a proper inclined position. With the free hand, load the blood collection tube holder with the desired blood collection tube. The blood collection tube is vacuum sealed, thus piercing the tube with the multiple sample needle of the needle adaptor breaks the seal and blood is drawn into the tube. Release the tourniquet as soon as the blood begins to enter the tube. When the tube ceases to fill with blood, remove the tube from the holder and invert the tube five times to mix the additives contained in the tube with the blood sample drawn, and successive samples may be drawn according to the aforementioned procedure until the desired number of samples are collected. Place gauze with a little pressure applied on the puncture site while quickly withdrawing the mosquito needle. Using the free hand, stab the mosquito needle into the needle disposal pit immediately after its withdrawal to avoid accidental needle strikes. Maintain pressure on the gauze until the puncture ceases to bleed and apply a bandage. Label the tube(s) with the DATE and TIME of collection, and the NAME of the patient and physician. Unscrew the needle from the needle adaptor, remove the mosquito needle from the disposal pit, and place both needles in biohazard cardboard. Place the tube(s), along with the used gloves, gauze, alcohol swab, and other blood collection aids into a lab container without delay and dispose of the needles in a conventional manner.

Accordingly, one object of the present invention is to provide a phlebotomy device which may be either self administered or administered by a health care professional.

Another object of the present invention is to provide a phlebotomy device which reduces complications involved in difficult phlebotomies such as rolling veins, tiny veins, and traumatic patients.

Another object of the present invention is to provide a phlebotomy device which ensures the fast and accurate filling of the sample tube without frothing or aerating, thereby maintaining the freshness and the integrity of the blood sample.

Still, another object of the present invention is to provide a phlebotomy device which reduces the risk of unwanted needle strike, both to the patient and the health care worker.

Further, an object of the present invention is to provide a phlebotomy device which is portable and convenient to use.

These and other objects of the present invention will become readily apparent upon further review of the following specification and drawings.

BRIEF DESCRIPTION OF THE DRAWINGS

FIG. 1 is an environmental perspective view of the present invention.

FIG. 2 is a perspective view of the present invention.

FIG. 3 is a bottom plan view of the mosquito needle, and the accompanying plastic wings, stilt adhesive, and hub.

Similar reference characters denote corresponding features consistently throughout the attached drawings.

DETAILED DESCRIPTION OF THE PREFERRED EMBODIMENT

Figure 4:
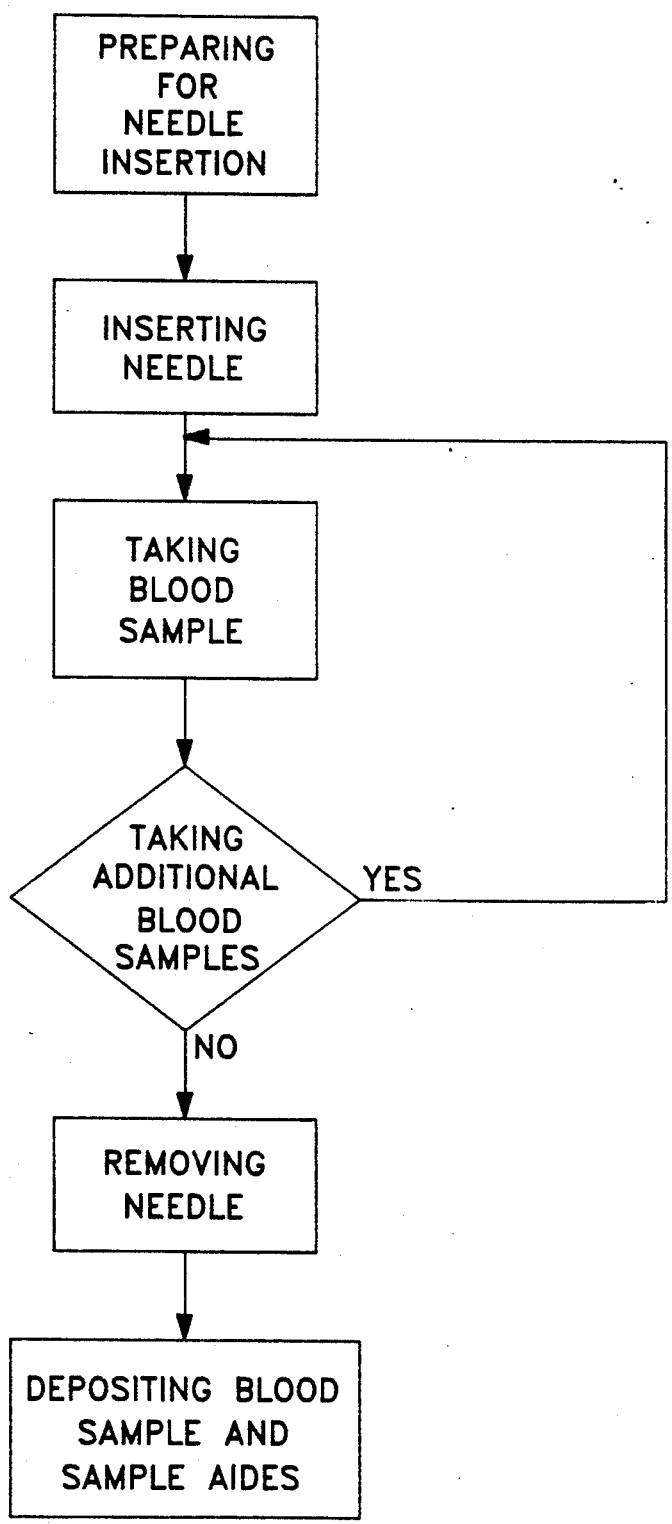
FIG. 4 represents a block diagram of the method of the present invention.

Now referring to the drawings, FIG. 1 shows the phlebotomy device 10 in use. The device 10 is comprised of a stand 12 having a blood collection tube holder 14 for retaining a blood collection tube 16. The blood collection tube holder 14 is partially housed within stand 12 and releasably attached to the stand 12 at a 25 degree angle to provide a fast and accurate filling of the blood collection tube 16 without frothing and aerating. The stand 12 is preferably transparent, either colored or colorless, to permit the user to see that the proper connections are made and that the blood is flowing through the device 10 properly. Finger grips 18 at the proximal end of the blood collection tube holder 14 ensure stability and enable the blood collection tube 16 to be inserted therein with the free hand (not shown) during the administration of the phlebotomy, thus allowing the same free hand (not shown) to adjust the tourniquet 22. Successive tests can be conducted, each requiring the use of different blood sample tubes 16, 16a, 16b. For example, a tube 16 with a red stopper 24 is used to draw blood samples for chemistry tests, a tube 16a with a violet stopper 24a is used to draw blood samples for hematology tests, and a tube 16b with a gray stopper 24b is used to draw blood samples for glucose and diabetes tests. The tubes 16, 16a, 16b are vacuum sealed. When the stoppers 24, 24a, 24b of the respective tubes 16, 16a, 16b are each punctured and penetrated by a proximal end of a multiple sample needle 26 protruding interiorly of the tube holder 14, the seal is broken and blood is drawn into the respective tube 16, 16a, 16b. The successive blood samples are made possible by the multiple sample needle 26 which is removably fastened or threadably attached to the distal end of the tube holder 14 via a needle adapter 28.

FIGS. 1 and 2 show the stand 12 further including an orifice or a needle disposal pit 27 adjacent the top thereof. The needle disposal pit 27 has inserted therein a replaceable pliable material 29, preferably hypochlorite clay, for the insertion and retention of contaminated mosquito needles 30. The mosquito needle 30 is an element of a proboscis set which, in addition to the stand 12, is included as part of the phlebotomy device 10. Prior to use, the mosquito needle 30 is shielded by a shield 48 (shown in FIG. 3) to prevent accidental needle strikes. Remove the shield 48 to insert the mosquito needle 30 which is insertable into the vein of the patient 20. The mosquito needle 30 is supported by a pair of plastic wings 34 at an angle approximately 15 degrees with the vein. The plastic wings 34 stabilize and secure the mosquito needle 30 to the arm of the patients 20 by stilt adhesive strips 36 which are exposed by peeling off the protective strips 38. A channel 44 is axially disposed interiorly of the mosquito needle 30 to permit the passage of blood therethrough. The proximal end of the mosquito needle 30 includes a hub 40 which is releasably connected to the distal end of a snout 42a. As seen in FIG. 2, snout 42a is housed within stand 12. The snout 42 is routed through a snout holder 32 adjacent the bottom edge of the stand 12 and the proximal end of the snout 42b is releasably connected to the distal end of the needle adaptor 28. With the needle adaptor 28 threadably attached to the blood collection tube holder 14, the multiple sample needle 26 is disposed axially interiorly of the distal portion of the blood collection tube holder 14.

FIG. 3 shows the detail of the mosquito needle 30 including the plastic wings 34, having stilt adhesive 36 exposable by removing the protective strips 38, and a hub 40. The plastic wings 34 are foldable along the phantom lines to incline and maintain the mosquito needle 30 at the proper angle to provide a structure similar to that shown in FIGS. 1 and 2.

The application of the device is fundamental. As shown in FIG. 4, prepare for the insertion of the mosquito needle 30, insert the mosquito needle 30, and collect a blood sample. Successive samples may be collected. When the desired sample or samples have been collected, the mosquito needle 30 is removed and the blood sample(s) and sample aids are deposited in a conventional manner.

Figures 4A, 4B, 4C:
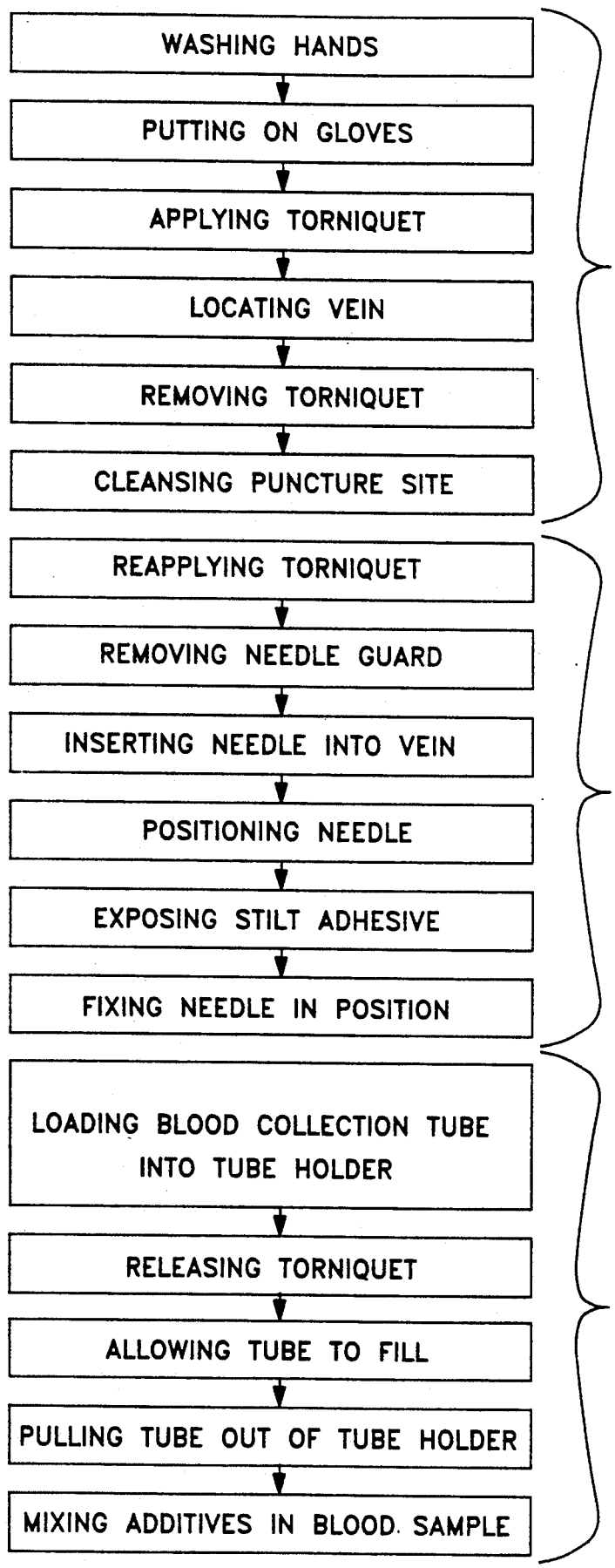
FIG. 4A is a block diagram of the steps of the PREPARING FOR NEEDLE INSERTION step.
FIG. 4B is a block diagram of the steps of the INSERTING NEEDLE step.
FIG. 4C is a block diagram of the steps of the TAKING BLOOD SAMPLE step.

FIG. 4A details the preparation step. Wash the hands thoroughly with soap and water and apply sterilized gloves. Tie a tourniquet 22 lightly to the biceps approximately two inches above the elbow such that it may be easily released. Locate the vein or puncture site and release the tourniquet 22. Cleanse the puncture site with an alcohol swab. Note that the tourniquet 22 should not be applied for more than a 60 second period.

The steps required to complete the insertion step are described in FIG. 4B. After the puncture site has been located and cleansed (see FIG. 4A), reapply the tourniquet 22 and remove the needle guard 48 to expose the beveled tip 33 of the mosquito needle 30. Insert the mosquito needle 30 into the vein with the beveled tip 33 pointing up in such a manner that the mosquito needle 30 is inserted directly in the top portion of the vein following the vein route. When the vein is entered, blood will appear at the hub 40. Position the mosquito needle 30 towards the arm of the patient 20 and hold the mosquito needle 30 steady as the stilt adhesive strips 36 are exposed. Allow the stilt adhesive strips 36 to stick to the arm of the patient 20, thus fixing the position of the mosquito needle 30 at the proper angle.

FIG. 4C shows the steps involved in taking the blood samples. With the free hand, load the tube holder 14 using the thumb to push the desired blood collection tube 16, 16a, 16b gently downwards deliberately puncturing the stopper 24, 24a, 24b and breaking the vacuum seal. With the seal broken, blood will enter into the tube 16, 16a, 16b. Continue to ease the tube 16, 16a, 16b into the tube holder 14 until the tube 16, 16a, 16b meets the interior distal end of the tube holder 14. Release the tourniquet 22. When the tube 16, 16a, 16b ceases to fill with blood, pull the tube 16, 16a, 16b out of the tube holder 14 with the free hand. Immediately invert the tube 16, 16a, 16b five times, gently twisting the hand, to mix the additives. Do not mix vigorously. At this point, additional blood samples may be taken if desired.

Figure 4D:
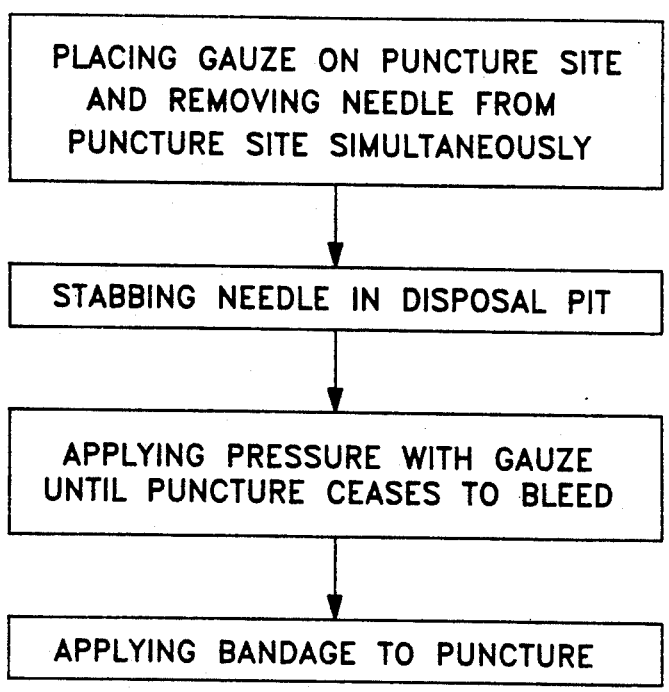
FIG. 4D is a block diagram of the steps of the REMOVING NEEDLE step.

After the desired blood samples are collected, the mosquito needle 30 is removed following the steps described in FIG. 4D. This is accomplished by placing gauze on the puncture site while quickly and simultaneously removing the mosquito needle 30 from the vein. Without hesitation, stab the mosquito needle 30 into the needle disposal pit 29 to avoid accidental needle strike. Apply pressure to the puncture wound with gauze until the bleeding stops, then apply a bandage.

Figure 4E:
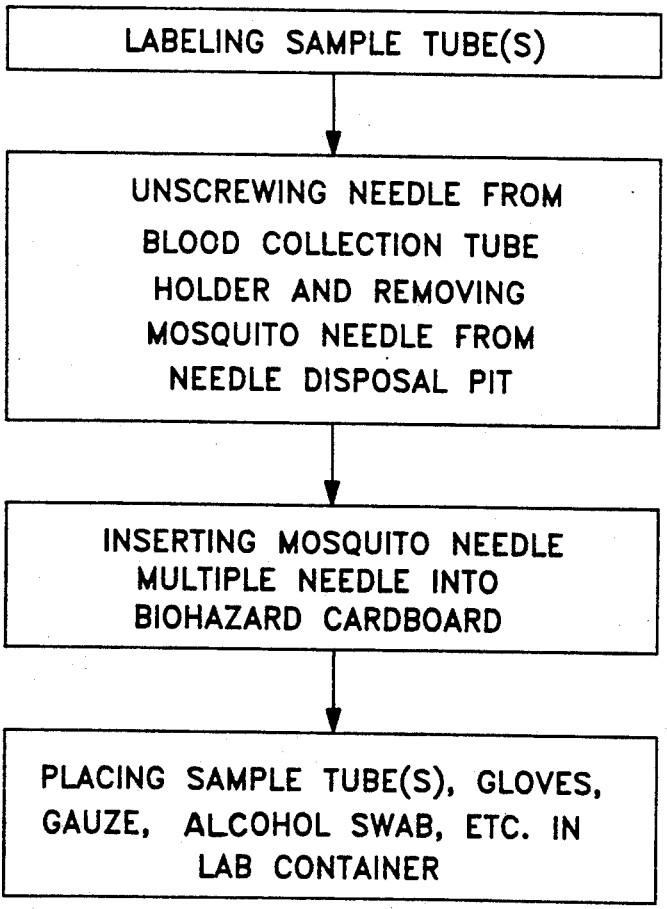
FIG. 4E is a block diagram of the steps of the DEPOSITING BLOOD SAMPLE AND SAMPLE AIDS step.

Finally, the blood sample(s) and sample aids are deposited in the proper manner as shown in FIG. 4E. Label the tube(s) 16, 16a, 16b with the TIME and DATE of the collection, and the NAME of the patient and physician. Unscrew the multiple sample needle 26 from the tube holder 14 and remove the mosquito needle 30 from the disposal pit 28. Carefully place both needles 26, 30 in biohazard cardboard. Deposit the tube(s) 16, 16a, 16b along with the gloves, the alcohol swab, the gauze, and other blood collection aids in the nearest lab container without delay. Dispose of the needles 26, 30 in a conventional manner.

It is to be understood that the present invention is not limited to the sole embodiment described above, but encompasses any and all embodiments within the scope of the following claims.

I claim:

1. A phlebotomy device to be used with a vacuum sealed blood collection tube for collecting blood samples from a vein of a patient, said device comprising:
   a) a stand including:
      1) a blood collection tube holder releasably attached thereto; and
      2) a needle disposal pit having a replaceable pliable substance inserted therein;
      3) a snout holder juxtaposed a bottom edge; and
   b) a proboscis set comprising:
      1) a needle adapter having a proximal end releasably attachable to a distal end of said blood collection tube holder, having a multiple sample needle protruding from said proximal end of said needle adapter axially and interiorly of said blood collection tube holder, and having a hub located at a distal end;
      2) a mosquito needle including:
         a) a beveled tip insertable into the vein of the patient;
         b) a pair of plastic wings having stilt adhesive strips juxtaposed a bottom surface exposable by removing a pair of respective protective strips, said pair of wings are flexible to form an inclined structure and said pair of stilt adhesive strips, having said pair of protective strips removed, stick to the patient to stabilize and secure said mosquito needle in an inclined position;
         c) an axial channel communicating with said beveled tip to facilitate passage of blood;
         d) a hub adjacent a distal end; and
      3) a snout joining said needle adapter to said mosquito needle, said snout having a proximal end connected to said hub of said needle adapter, being routed through said snout holder, and having said distal end connected to said hub of said mosquito needle, wherein said needle adapter is attached to said blood collection tube holder, said snout joins said needle adapter and said mosquito needle, said mosquito needle is inserted into the vein of the patient, and the blood collection tube is inserted into a proximal end of said blood collection tube holder piercing the vacuum seal and drawing a sample of blood from the vein of the patient into the blood collection tube.

2. The device according to claim 1, wherein said stand is transparent to allow the user to observe the connection of said snout to said hub of said needle adapter and to observe the flow of blood through the device.

3. The device according to claim 1, wherein said blood collection tube holder is releasably attached to said stand at an angle 25 degrees relative to an axis horizontal to said bottom edge of said stand.

4. The device according to claim 1, wherein said holder is provided with finger grips disposed adjacent said proximal end to offer stability and control of a single handed insertion of the blood collection tube into said blood collection tube holder.

5. The device according to claim 1, wherein said pliable substance includes hypochlorite clay.

6. The device according to claim 1, wherein said needle adapter is threadably attached to said blood collection tube holder.

7. The device according to claim 1, wherein said proboscis set is disposable.

8. The device according to claim 1, further comprising a shield removably attached to said mosquito needle to surround said beveled tip located adjacent a distal end, thus reducing the risk of an accidental needle strike.

9. The device according to claim 1, wherein said inclined structure formed by said plastic wings provides an incline which is 15 degrees with a horizontal relative to the vein.

10. A method of using a phlebotomy device with vacuum sealed blood collection tubes for collecting blood samples from a vein of a patient, said method comprising the following steps:
   a) preparing for the insertion of a mosquito needle comprising the following steps:
      1) washing the user's hands thoroughly with soap and water;
      2) putting a pair of gloves on the cleansed hands;
      3) applying a tourniquet lightly on the patient's biceps such that the tourniquet can be removed with one hand;
      4) locating a puncture site;
      5) removing the tourniquet from the patient's biceps; and
      6) cleansing the puncture site with an alcohol swab;
   b) inserting the mosquito needle comprising the following steps:
      1) reapplying the tourniquet to the patient's biceps;
      2) removing a needle guard from the mosquito needle to expose a beveled tip;
      3) inserting the mosquito needle into a top portion of the vein of the patient along the vein route with the beveled tip pointing upwards;
      4) positioning the mosquito needle at a proper angle with the vein and with a pair of stilt adhesive strips on a bottom surface of a pair of wings which are configured to maintain the position of the mosquito needle;
      5) exposing the stilt adhesive by removing a pair of protective strips concealing the pair of stilt adhesive strips; and
      6) fixing the mosquito needle in position by allowing the pair of stilt adhesive strips to contact the patient's skin;
   c) taking blood samples comprising the following steps:
      1) loading a vacuum sealed blood collection tube into a proximal end of a blood collection tube holder with an unoccupied hand, there being a conduit connecting the mosquito needle to the tube holder, using a thumb to push the blood collection tube downwards puncturing a rubber stopper juxtaposed a distal end thereof, thus breaking the vacuum seal allowing the blood collection tube to draw a sample of blood from the patient, the tube holder having a multiple sample needle threadably attached thereto to break the seal;
      2) releasing the tourniquet from the biceps;
      3) allowing the blood collection tube to fill until blood ceases to flow;
      4) pulling the blood collection tube out of the blood collection tube holder; and
      5) mixing the collected blood with additives by gently inverting the blood collection tube five times with a twisting motion of the hand immediately after removing the same from the blood collection tube holder; and repeating step c as needed to obtain multiple blood samples;
   d) removing the mosquito needle comprising the following steps:
      1) placing gauze on the puncture site and removing the mosquito needle from the puncture site simultaneously;
      2) stabbing the mosquito needle into a needle disposal pit immediately after removing the same from the puncture site;
      3) applying pressure with gauze to the puncture site until the bleeding from the puncture site stops; and
      4) applying a bandage to the puncture site; and
   e) depositing blood samples and sample aids comprising the following steps;
      1) labeling the collection tubes with the date and time of the collection, and with the name of the patient and physician;
      2) removing the multiple sample needle screwed to the blood collection tube holder and removing the mosquito needle from the needle disposal pit; and
      3) inserting the multiple needle and the mosquito needle into biohazard cardboard for proper disposal; and
      4) placing the collection tubes, the gloves, and the alcohol swab in a lab container.

11. The method according to claim 10, wherein the tourniquet is applied to the biceps of the patient approximately two inches above the elbow.

12. The method according to claim 10, wherein the mosquito needle is positioned at an incline of 15 degrees relative to an axis horizontal to the vein being punctured.

* * * * *